United States Patent
Kim et al.

(10) Patent No.: US 11,498,946 B2
(45) Date of Patent: Nov. 15, 2022

(54) PHARMACEUTICAL COMPOSITION FOR COMBINATION THERAPY FOR PREVENTING OR TREATING CANCER CONTAINING TUMOR-SPECIFIC DRUG CONJUGATE AND ANTI-PD-L1 ANTIBODY AS ACTIVE INGREDIENTS

(71) Applicant: KOREA INSTITUTE OF SCIENCE AND TECHNOLOGY, Seoul (KR)

(72) Inventors: Kwangmeyung Kim, Seoul (KR); Ju Hee Ryu, Seoul (KR); Hong Yeol Yoon, Seoul (KR); Man Kyu Shim, Seoul (KR); Suah Yang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 33 days.

(21) Appl. No.: 17/118,767

(22) Filed: Dec. 11, 2020

(65) Prior Publication Data
US 2021/0179681 A1    Jun. 17, 2021

(30) Foreign Application Priority Data
Dec. 11, 2019    (KR) .......................... 10-2019-0164258

(51) Int. Cl.
| | |
|---|---|
| *C07K 14/47* | (2006.01) |
| *A61P 35/00* | (2006.01) |
| *A61K 47/10* | (2017.01) |
| *C07K 16/28* | (2006.01) |
| *A61K 47/64* | (2017.01) |

(52) U.S. Cl.
CPC .......... *C07K 14/4703* (2013.01); *A61K 47/10* (2013.01); *A61K 47/64* (2017.08); *A61P 35/00* (2018.01); *C07K 16/2827* (2013.01)

(58) Field of Classification Search
None
See application file for complete search history.

(56) References Cited

U.S. PATENT DOCUMENTS

| | | | |
|---|---|---|---|
| 6,245,358 B1 * | 6/2001 | Adami | ................. A61P 35/00 424/423 |
| 2019/0083637 A1 * | 3/2019 | Kim | ................. A61K 47/65 |

FOREIGN PATENT DOCUMENTS

| | | | | |
|---|---|---|---|---|
| KR | 101930399 B1 | | 12/2018 | |
| WO | WO-2016075174 A1 * | | 5/2016 | ........... A61K 31/704 |

* cited by examiner

*Primary Examiner* — Christina Bradley
(74) *Attorney, Agent, or Firm* — Rabin & Berdo, P.C.

(57) ABSTRACT

The present disclosure relates to a pharmaceutical composition for combination therapy for preventing or treating cancer, which contains a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; as active ingredients. The pharmaceutical composition significantly inhibits cancer growth in in-vivo experiments and exhibits an effect of significantly enhancing immunotherapeutic effect by activating immune cells in cancerous tissues.

In particular, the pharmaceutical composition for combination therapy according to the present disclosure has superior tumor accumulation efficiency and selectivity as compared to existing anticancer agents, and is very stable with little toxicity to normal tissues other than cancerous tissues.

4 Claims, 6 Drawing Sheets
Specification includes a Sequence Listing.

PHARMACEUTICAL COMPOSITION FOR COMBINATION THERAPY FOR PREVENTING OR TREATING CANCER CONTAINING TUMOR-SPECIFIC DRUG CONJUGATE AND ANTI-PD-L1 ANTIBODY AS ACTIVE INGREDIENTS

CROSS-REFERENCE TO RELATED APPLICATIONS

This application claims, under 35 U.S.C. § 119, the priority of Korean Patent Application No. 10-2019-0164258 filed on Dec. 11, 2019 in the Korean Intellectual Property Office, the disclosure of which is incorporated herein by reference in its entirety.

SEQUENCE LISTING

This application contains a Sequence Listing submitted via EFS-Web and hereby incorporated by reference in its entirety. The Sequence Listing is named SEQCRF-CHIP-180.txt, created on Jan. 12, 2021, and 5,593 bytes in size.

TECHNICAL FIELD

The present disclosure relates to a pharmaceutical composition for combination therapy for preventing or treating cancer, which contains a tumor-specific drug conjugate and an anti-PD-L1 antibody as active ingredients, and a method for treating cancer using the same.

BACKGROUND

Colorectal cancer has no symptom in the early stage, and symptomatic cases are often impossible to treat because the cancer has already progressed severely. Although complete treatment can be anticipated if it is found at an early stage, the risk is very high if detected later due to metastasis to parts difficult to excise, such as the lungs, liver, lymph nodes, peritoneum, etc.

In addition, colorectal cancer has high recurrence rate. It is known that the recurrence rate is about 70% in 12-24 months after surgery, and 90% in 3-5 years after surgery. In addition, since colorectal cancer shows the highest prevalence rate among cancers, development of treatment methods is imminent.

Although various therapeutic agents for treating cancers such as colorectal cancer have been developed recently, they have problems that clinical effectiveness cannot be expected or long-term treatment is difficult due to side effects.

Recently, Immune checkpoint blockade with antibodies inhibiting the PD-1/PD-L1 interaction, is the most promising approach for cancer immunotherapy. However, these therapeutic agents are costly for their efficient effects and it is reported that autoimmune diseases occur when they are used at high doses to increase the therapeutic effect due to excessively enhanced immune function. Accordingly, there still is a need for an improved drug for treating colorectal cancer.

REFERENCES OF THE RELATED ART

Patent Documents

Patent document 1. Korean Patent Registration Publication No. 10-1930399.

SUMMARY

The present disclosure is directed to providing a pharmaceutical composition for combination therapy for preventing or treating cancer.

The present disclosure is also directed to providing a pharmaceutical composition for animals for treating or preventing cancer.

The present disclosure is also directed to providing a method for treating cancer by administering the composition to human or a non-human animal.

The present disclosure is also directed to providing a method for inhibiting metastasis and recurrence of colorectal cancer cells by killing colorectal cancer cells and activating immune cells around the colorectal cancer cells.

The present disclosure is also directed to providing a novel use for preparation of a drug or a drug for animals for treating or preventing cancer.

In an aspect, the present disclosure provides a pharmaceutical composition for combination therapy for preventing or treating cancer, which contains a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; as active ingredients.

The pharmaceutical composition for combination therapy may be in the form of a mixture of the first pharmaceutical ingredient and the second pharmaceutical ingredient, or the first pharmaceutical ingredient and the second pharmaceutical ingredient may be prepared independently and administered simultaneously or sequentially.

In the first pharmaceutical ingredient, a weight ratio of the drug conjugate and the poloxamer may be 1:0.1 to 1:0.5.

A weight ratio of the first pharmaceutical ingredient and the second pharmaceutical ingredient may be 1:0.1 to 1:0.8.

The anti-PD-L1 antibody may be one or more selected from a group consisting of BMS-936559, avelumab, durvalumab, atezolizumab and a combination thereof.

The cancer may be one or more selected from a group consisting of breast cancer, uterine cancer, fallopian tube cancer, ovarian cancer, stomach cancer, brain cancer, rectal cancer, colorectal cancer, small intestine cancer, esophageal cancer, lymphatic cancer, gallbladder cancer, lung cancer, skin cancer, kidney cancer, bladder cancer, blood cancer, pancreatic cancer, prostate cancer, thyroid cancer, endocrine gland cancer, oral cancer and liver cancer.

In another aspect, the present disclosure provides a method for treating cancer, which includes administering a therapeutically effective amount of a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; to human or a non-human mammal.

The cancer may be colorectal cancer.

The first pharmaceutical ingredient may be administered intravenously and the second pharmaceutical ingredient may be administered intraperitoneally.

In another aspect, the present disclosure provides a method for inhibiting metastasis and recurrence of colorectal cancer cells by killing colorectal cancer cells and activating immune cells around the colorectal cancer cells, which includes a step of administering a therapeutically effective amount of a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; to human or a non-human mammal.

The pharmaceutical composition for combination therapy according to the present disclosure provides significantly superior effect of treating, preventing and alleviating cancer as compared to single therapies.

In particular, the pharmaceutical composition for combination therapy according to the present disclosure has superior tumor accumulation efficiency and selectivity as compared to existing anticancer agents, and is very stable with little toxicity to normal tissues other than cancerous tissues.

DETAILED DESCRIPTION OF EMBODIMENTS

Figure 1:
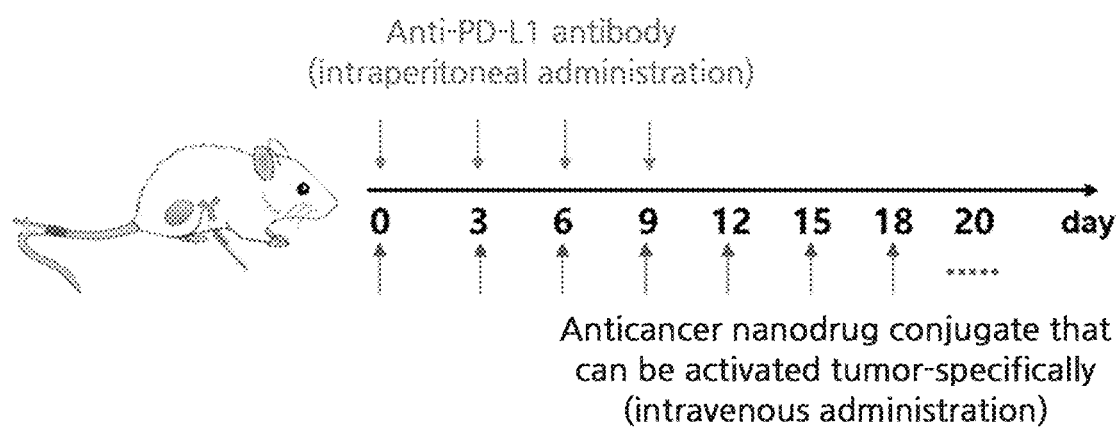
FIG. 1 schematically illustrates the administration method and cycle of a combination therapy of a formulated drug conjugate (FDOX) and an anti-PD-L1 antibody.

Hereinafter, the present disclosure is described in detail.

As described above, although anti-PD-L1 antibodies, which are the immune checkpoint inhibitors most frequently used in clinical applications, were developed recently, these therapeutic agents are costly for their effects and it is reported that autoimmune diseases occur when they are used at high doses to increase the therapeutic effect due to excessively enhanced immune function. Therefore, the use of the therapeutic agents is limited.

A combination therapy of the anti-PD-L1 antibody and an anticancer agent (doxorubicin, paclitaxel, oxaliplatin, etc.) was developed. Although anticancer activity was increased to some extent, it was found out that severe systemic toxicity was induced, resulting in severe side effects of damaging the normal tissues of patients.

Accordingly, the present disclosure is directed to providing a new pharmaceutical composition with superior accumulation efficiency in tumors while having remarkably decreased toxicity as compared to existing anticancer agents.

An aspect of the present disclosure relates to a pharmaceutical composition for combination therapy for preventing or treating colorectal cancer, which contains a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; as active ingredients.

According to an exemplary embodiment of the present disclosure, an effective amount of the first pharmaceutical ingredient containing a drug conjugate wherein an anticancer agent is bound at one end of an amphiphilic peptide represented by SEQ ID NO 1 and a poloxamer and an effective amount of the second pharmaceutical ingredient containing an anti-PD-L1 antibody of the pharmaceutical composition for combination therapy may be mixed and administered simultaneously.

According to another exemplary embodiment of the present disclosure, the pharmaceutical composition for combination therapy may be in the form of a mixture of the first pharmaceutical ingredient and the second pharmaceutical ingredient, or the first pharmaceutical ingredient and the second pharmaceutical ingredient may be prepared independently and administered simultaneously or sequentially. In this case, the pharmaceutical composition for combination therapy may be a pharmaceutical composition for combination therapy for simultaneous or sequential administration of the first pharmaceutical ingredient containing an effective amount of a drug conjugate wherein an anticancer agent is bound at one end of an amphiphilic peptide represented by SEQ ID NO 1 and a poloxamer and the second pharmaceutical ingredient containing an effective amount of an anti-PD-L1 antibody as active ingredients. For the sequential administration, the sequence of administration is not particularly limited.

In addition, the present disclosure may provide a kit for preventing or treating colorectal cancer, which contains a first pharmaceutical ingredient containing an effective amount of a drug conjugate wherein an anticancer agent is bound at one end of an amphiphilic peptide represented by SEQ ID NO 1 and a poloxamer and a second pharmaceutical ingredient containing an effective amount of an anti-PD-L1 antibody as active ingredients For individual or sequential administration of the first pharmaceutical ingredient and the second pharmaceutical ingredient, they may be prepared in separate containers or in the same container.

The present disclosure provides not only significantly improved anticancer effect but also remarkably superior effect of activating immune cells as compared to single administration through co-administration of the first pharmaceutical ingredient containing a drug conjugate wherein an anticancer agent is bound at one end of an amphiphilic peptide represented by SEQ ID NO 1 and a poloxamer; and the second pharmaceutical ingredient containing an anti-PD-L1 antibody.

In addition, the pharmaceutical composition for combination therapy is very stable with no cytotoxicity at all to normal tissues since it has toxicity specifically to cancerous tissues and activates immune cells.

In addition, when compared with single administration or co-administration with the existing anticancer agent or anti- PD-L1 antibody, an effect beyond a synergistic effect can be achieved since the growth of cancerous tissues can be inhibited remarkably for a long period of time.

In the present disclosure, the term "peptide" refers to a linear molecule formed as amino acid residues are linked by peptide bonds.

For reference, representative amino acids and their abbreviations are as follows: alanine (Ala, A), isoleucine (Ile, I), leucine (Leu, L), methionine (Met, M), phenylalanine (Phe, F), proline (Pro, P), tryptophan (Trp, W), valine (Val, V), asparagine (Asn, N), cysteine (Cys, C), glutamine (Gln, Q), glycine (Gly, G), serine (Ser, S), threonine (Thr, T), tyrosine (Try, Y), aspartic acid (Asp, D), glutamic acid (Glu, E), arginine (Arg, R), histidine (His, H), lysine (Lys, K).

The drug conjugate according to the present disclosure may be one wherein an amphiphilic peptide specifically cleaved by the cathepsin B enzyme is bound to an anticancer agent. Through the interaction between the amphiphilic peptide and the anticancer agent, the cleavage by the cathepsin B enzyme leads to the formation of the cleaved amphiphilic peptide and the anticancer agent partly bound thereto. Therefore, the drug conjugate according to the present disclosure may be usefully used to achieve superior effect on tumor cells.

The drug conjugate is present as spherical particles in solution through self-assembly, but the size is not uniform and it is somewhat unstable in vivo. However, according to the present disclosure, in-vivo stability can be ensured and administration with an accurate dosage is possible by mixing the drug conjugate with a poloxamer.

The cathepsin B enzyme is specifically expressed in tumor cells, particularly in metastatic cancers, although its expression is limited in normal cells. The drug conjugate of the present disclosure, which is co-administered with the anti-PD-L1 antibody, exhibits an effect of preventing or treating colorectal cancer among cancers, most specifically metastatic colorectal cancer.

The anticancer agent may be any one selected from a group consisting of Taxol, bendamustine, busulfan, busulfan, chlorambucil, cyclophosphamide, dacarbazine, Adriamycin (doxorubicin), daunomycin, ifosfamide, melphalan, procarbazine, streptozocin, temozolomide, asparaginase, capecitabine, cytarabine, 5-fluorouracil, fludarabine, gemcitabine, methotrexate, pemetrexed, raltitrexed, actinomycin D, bleomycin, bleomycin, doxorubicin, pegylated liposomal doxorubicin, epirubicin, idarubicin, mitomycin, mitoxantrone, etoposide, docetaxel, irinotecan, paclitaxel, topotecan, vinblastine, vincristine, vinorelbine, carboplatin, cisplatin, oxaliplatin, alemtuzumab, BCG, bevacizumab, cetuximab, denosumab, erlotinib, gefitinib, imatinib, interferon, ipilimumab, lapatinib, panitumumab, rituximab, sunitinib, sorafenib, temsirolimus, trastuzumab, clodronate, ibandronate, pamidronate and zoledronic acid. Specifically, it may be doxorubicin.

In the present disclosure, the drug conjugate may be specifically represented by Structural Formula 1.

[Structural Formula 1]

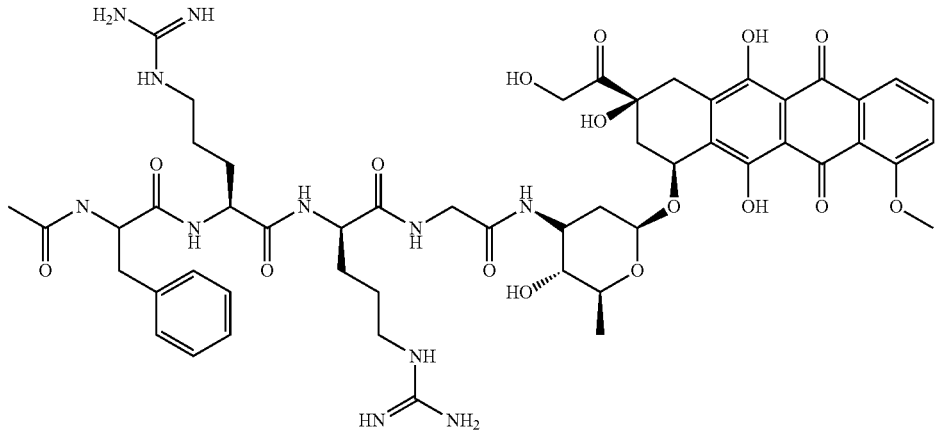

Specifically, the poloxamer may be poloxamer 188 (pluronic F68).

In the first pharmaceutical ingredient, a weight ratio of the drug conjugate and the poloxamer may be 1:0.1 to 1:0.5, specifically 1:0.2 to 1:0.4, most specifically 1:0.3 to 1:0.35.

The first pharmaceutical ingredient may be prepared by mixing the drug conjugate and the poloxamer at the above-described weight ratio, and may be in the form of an emulsion of spherical particles with an average diameter of 80-200 nm. Specifically, the dispersity may be below 0.2. If other additives are used instead of the poloxamer or if the mixing weight ratio is outside the above-described range, an emulsion of spherical particles with an average diameter of 80-200 nm and a dispersity below 0.2 cannot be obtained.

If the average diameter of the first pharmaceutical ingredient is smaller than 80 nm, the drug conjugate may be degraded easily in vivo due to insufficient stability. And, if the dispersity is 0.2 or higher, accurate dosage control may be difficult due to non-uniformity.

The first pharmaceutical ingredient remains very stable in vivo but, in the presence of the cathepsin B enzyme of tumor cells, the amphiphilic peptide of the drug conjugate is cleaved and the anticancer agent of the drug conjugate is released from the core part of the nanoparticle.

In the present disclosure, the term "PD-L1" refers to one of two cell surface glycoprotein ligands (the other being PD-L2) for PD-1, which binds to PD-1 and downregulates T cell activation and cytokine secretion. As used in the present disclosure, the term "PD-L1" encompasses human PD-L1 (hPD-L1), variants, isoforms and species homologues of hPD-L1, and analogues having at least one common epitope with hPD-L1. The complete sequence of hPD-L1 can be found under GenBank Accession No. Q9NZQ7. In some exemplary embodiments, the PD-L1 is human PD-L1 having an amino acid sequence represented by SEQ ID NO 2 or SEQ ID NO 3. The PD-L1 (programmed death-ligand 1) also refers to a protein encoded by the CD274 gene and is also known as CD274 or B7-H1 (B7 homolog 1).

The anti-PD-L1 antibody refers to an antibody which inhibits PD-L1 signaling by binding to PD-L1. In some exemplary embodiments, the anti-PD-L1 antibody may block the binding of PD-1 to PD-L1 by binding to PD-L1, or may inhibit PD-1 and bind to PD-L1.

In the present disclosure, the term "antibody" refers to a molecule containing at least hypervariable regions (HVRs) H1, H2 and H3 of heavy chains and L1, L2 and L3 of light chains, wherein the molecule is capable of binding to an antigen. The term antibody includes, but is not limited to, fragments that are capable of binding to an antigen, such as Fv, single-chain Fv (scFv), Fab, Fab' and (Fab')$_2$. The term antibody also includes, but is not limited to, chimeric antibodies, humanized antibodies, human antibodies, and antibodies of various species such as mouse, human, cynomolgus monkey, etc. It also includes antibodies conjugated to other molecules such as molecule drugs, bispecific antibodies and multispecific antibodies.

In the present disclosure, the term "heavy chain variable region" refers to a region including heavy chain HVR1, framework (FR)2, HVR2, FR3 and HVR3. In some exemplary embodiments, the heavy chain variable region also includes at least a portion of FR1 and/or at least a portion of FR4.

In the present disclosure, the term "heavy chain constant region" refers to a region including at least three heavy chain constant domains, CH1, CH2 and CH3. Nonlimiting exemplary heavy chain constant regions include γ, δ and α. And, nonlimiting exemplary heavy chain constant regions include ε and μ. Each heavy chain constant region corresponds to an antibody isotype. For example, an antibody including a γ constant region is an IgG antibody, an antibody including a δ constant region is an IgD antibody, and an antibody including an α constant region is an IgA antibody. Further, an antibody including a μ constant region is an IgM antibody, and an antibody including an ε constant region is an IgE antibody. Certain isotypes can be further subdivided into subclasses. For example, IgG antibodies include, but are not limited to, IgG1 (including a γ1 constant region), IgG2 (including a γ2 constant region), IgG3 (including a γ3 constant region) and IgG4 (including a γ4 constant region) antibodies; IgA antibodies include, but are not limited to, IgA1 (including an α1 constant region) and IgA2 (including an α2 constant region) antibodies; and IgM antibodies include, but are not limited to, IgM1 and IgM2.

In the present disclosure, the term "heavy chain" refers to a polypeptide including at least a heavy chain variable region, with or without a leader sequence. In some exemplary embodiments, the heavy chain includes at least a portion of a heavy chain constant region. The term "full-length heavy chain" refers to a polypeptide including a heavy chain variable region and a heavy chain constant region, with or without a leader sequence.

In the present disclosure, the term "light chain variable region" refers to a region including light chain HVR1, framework (FR) 2, HVR2, FR3 and HVR3. For example, the light chain variable region includes FR1 and/or FR4.

In the present disclosure, the term "light chain constant region" refers to a region including a light chain constant domain $C_L$. Nonlimiting exemplary light chain constant regions include λ and κ.

In the present disclosure, the term "light chain" refers to a polypeptide including at least a light chain variable region, with or without a leader sequence. In some exemplary embodiments, the light chain includes at least a portion of a light chain constant region. In the present disclosure, the term "full-length light chain" refers to a polypeptide including a light chain variable region and a light chain constant region, with or without a leader sequence.

In the present disclosure, the term "hypervariable region" or "HVR" refers to each region of an antibody variable domain which is hypervariable in sequence and/or forms a structurally defined loop ("hypervariable loop"). In general, a native four-chain antibody includes six HVRs; three in $V_H$ (H1, H2 and H3), and three in $V_L$ (L1, L2 and L3). HVRs generally include amino acid residues from hypervariable loops and/or from complementarity-determining regions (CDRs), the latter being of highest sequence variability and/or being involved in antigen recognition. Exemplary hypervariable loops occur at amino acid residues 26-32 (L1), 50-52 (L2), 91-96 (L3), 26-32 (H1), 53-55 (H2) and 96-101 (H3) (Chothia and Lesk, J. Mol. Biol. 196: 901-917 (1987)). Exemplary CDRs (CDR-L1, CDRL2, CDR-L3, CDR-H1, CDR-H2 and CDR-H3) occur at amino acid residues 24-34 (L1), 50-56 (L2), 89-97 (L3), 31-35B (H1), 50-65 (H2) and 95-102 (H3) (Kabat et al., Sequences of Proteins of Immunological Interest, 5th Ed. Public Health Service, National Institutes of Health, Bethesda, Md. (1991)). The terms hypervariable regions (HVRs) and complementarity-determining regions (CDRs) both refer to portions of the variable region that form antigen-binding regions.

In the present disclosure, the term "humanized antibody" refers to an antibody in which at least one amino acid in a framework region of a non-human variable region has been replaced with the corresponding amino acid of a human variable region. In some exemplary embodiments, the humanized antibody includes at least one human constant region or a fragment thereof. In some exemplary embodiments, the humanized antibody is Fab, scFv, (Fab')2, etc.

In the present disclosure, the term "human antibody" refers to an antibody produced in human, an antibody produced in a non-human animal including a human immunoglobulin gene, e.g., XenoMouse, or an antibody selected using an in-vitro method, e.g., phage display, wherein the antibody repertoire is based on a human immunoglobulin sequence.

Specifically, the anti-PD-L1 antibody may be one or more selected from a group consisting of BMS-936559, avelumab, durvalumab, atezolizumab and a combination thereof, although not being specially limited thereto.

The BMS-936559 (MDX-1105) may be referred to, for example, in International Patent Publication No. WO2007/005874. Avelumab (MSB0010718C) is a fully human PD-L1 IgG1 monoclonal antibody developed by Merck and Pfizer. Durvalumab (MEDI4736) is an anticancer immunotherapeutic agent developed by AstraZeneca. Atezolizumab (MPDL3280A) is a fully humanized monoclonal antibody of IgG1 isotype against PD-L1, produced by Genentech/Roche.

The cancer may be one or more selected from a group consisting of breast cancer, uterine cancer, fallopian tube cancer, ovarian cancer, stomach cancer, brain cancer, rectal cancer, colorectal cancer, small intestine cancer, esophageal cancer, lymphatic cancer, gallbladder cancer, lung cancer, skin cancer, kidney cancer, bladder cancer, blood cancer, pancreatic cancer, prostate cancer, thyroid cancer, endocrine gland cancer, oral cancer and liver cancer. Specifically, it may be colorectal cancer.

The term pharmaceutically effective amount includes "therapeutically effective amount" and "prophylactically effective amount". The term "therapeutically effective amount" refers to an amount of a drug or a therapeutic agent capable of reducing the severity of the symptoms of a disease, increasing the frequency and duration of a period with no symptoms of a disease or preventing damage or disorder resulting from a disease, when used alone or in combination with another therapeutic agent. The term "prophylactically effective amount" refers to an amount of a drug that prevents the onset or recurrence of colorectal cancer in a subject with a risk of the cancer or a subject with a risk of pain due to recurrence of the cancer. The level of the effective amount may be determined depending on the type and severity of a disease, the age and sex of a subject, drug activity, sensitivity to the drug, administration time, administration route, excretion rate, treatment period, a drug to be used simultaneously and other factors well-known in the medical field.

The term "administration" used in the present disclosure refers to physical introduction of a composition into a subject using various methods and delivery systems known to those of ordinary skill in the art. Administration routes for the pharmaceutical composition of the present disclosure include all administration routes. Specifically, the pharmaceutical composition may be administered parenterally, e.g., intravenously, intramuscularly, subcutaneously, intraperitoneally, intraspinally or via other parenteral administration routes, such as injection or infusion. For example, the composition of the present disclosure may be administered once or multiple times and/or over one or more extended period.

Specifically, a weight ratio of the first pharmaceutical ingredient and the second pharmaceutical ingredient may be 1:0.1 to 1:0.8. If the weight ratio of the first pharmaceutical ingredient and the second pharmaceutical ingredient is below 1:0.1 or exceeds 1:0.8, the effect of inhibiting cancer, particularly colorectal cancer, and activating immune cells is decreased remarkably.

The administration dose of the pharmaceutical composition of the present disclosure may vary depending on the age, sex and body weight of a patient. Specifically, the composition of the present disclosure may be administered at a dose of 0.1-100 mg/kg, once to several times a day, depending on the severity of the disease of a subject with cancer. In addition, the administration dose may be increased or decreased depending on administration route, the severity of a disease, the sex, body weight and age of a patient, and particularly the severity of cancer of the patient.

In addition, the composition of the present disclosure may be administered as an individual therapeutic agent or in combination with another therapeutic agent. When administered with another therapeutic agent, the composition of the present disclosure and the another therapeutic agent may be administered sequentially or simultaneously. The another therapeutic agent may be a drug, e.g., a compound, a protein, etc., which facilitates cancer regression or additionally prevents tumor growth. In addition, various anticancer therapies other than drug therapy, such as radiation therapy, may be used.

Another aspect of the present disclosure relates to a pharmaceutical composition for treating or preventing cancer, which contains a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; as active ingredients.

In addition, the present disclosure relates to a pharmaceutical composition for animals for treating or preventing cancer, which contains a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; as active ingredients.

In addition, the present disclosure provides a method for treating cancer, which includes administering a therapeutically effective amount of a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; to human or a non-human mammal. Specifically, a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; may be administered to a subject having cancer.

In addition, the present disclosure provides a method for inhibiting metastasis and recurrence of colorectal cancer cells by killing colorectal cancer cells and activating immune cells around the colorectal cancer cells, which includes administering a therapeutically effective amount of a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; to human or a non-human mammal.

In addition, the present disclosure provides a novel use of a first pharmaceutical ingredient containing the drug conjugate wherein an anticancer agent is bound at one end of an amphiphilic peptide represented by SEQ ID NO 1 and a poloxamer; and a second pharmaceutical ingredient containing an anti-PD-L1 antibody; for preparation of a drug or a drug for animals for treating or preventing cancer.

The terms used in the description of the method for treating or preventing cancer according to the present disclosure have the same meaning as those described above in the description of the pharmaceutical composition for treating or preventing cancer, unless specially mentioned otherwise.

In the present disclosure, the term "subject" includes human or any non-human mammal. The term "non-human mammal" refers to a vertebrate, e.g., a non-human primate, sheep, dog or a rodent, e.g., mouse, rat or guinea pig. Specifically, the subject may be human. In the present disclosure, the term "subject" may be used interchangeably with "individual" or "patient".

For example, the treatment of cancer may inhibit tumor growth by about 10% or more, about 20% or more, about 40% or more, about 60% or more or about 80% or more as compared to a non-treated subject.

In the method for treating or preventing cancer according to the present disclosure, the first pharmaceutical ingredient and the second pharmaceutical ingredient may be administered to a subject simultaneously, sequentially or individually. The "simultaneous" administration means that the first pharmaceutical ingredient and the second pharmaceutical ingredient are administered at once through the same administration method.

The "sequential" administration means that the first pharmaceutical ingredient and the second pharmaceutical ingredient are administered by separate administration methods, relatively continuously, with as short an interval between the administrations as possible. The "individual" administration means that the first pharmaceutical ingredient and the second pharmaceutical ingredient are administered with a predetermined interval. The administration methods of the first pharmaceutical ingredient and the second pharmaceutical ingredient may be adequately selected by those skilled in the art in consideration of therapeutic effect and side effects.

Specifically, in the method for treating or preventing cancer according to the present disclosure, the first pharmaceutical ingredient may be administered intravenously and the second pharmaceutical ingredient may be administered intraperitoneally.

The cancer may be one or more selected from a group consisting of breast cancer, uterine cancer, fallopian tube cancer, ovarian cancer, stomach cancer, brain cancer, rectal cancer, colorectal cancer, small intestine cancer, esophageal cancer, lymphatic cancer, gallbladder cancer, lung cancer, skin cancer, kidney cancer, bladder cancer, blood cancer, pancreatic cancer, prostate cancer, thyroid cancer, endocrine gland cancer, oral cancer and liver cancer, specifically colorectal cancer, most specifically metastatic colorectal cancer.

According to an aspect of the present disclosure, when a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; are administered at therapeutically effective amounts, the growth, metastasis or recurrence of cancer can be inhibited effectively by inducing the death of cancer cells and activation of immune cells around the cancer cells without affecting other organs and normal tissues wherein no cancer has been formed. In Test Example 3, it was confirmed that cancer cells can be killed effectively by administering a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; thereby inducing the death of the cancer cells and activation of immune cells around the cancer cells. In particular, the present disclosure is particularly useful for treatment of a cancer exhibiting high metastasis to other organs or high recurrence rate and overexpression of the cathepsin B enzyme, such as colorectal cancer.

Hereinafter, the present disclosure will be described in further detail through example, etc. However, the scope and contents of the present disclosure are not reduced or limited by the examples, etc. In addition, it will be obvious that those of ordinary skill can easily carry out the present disclosure based on the disclosure of the present disclosure including the examples and that changes and modifications made thereto also belong to the scope of the attached claims.

Hereinafter are given the results of representative experiments.

Preparation Example 1

Synthesis of FRRG-DOX Drug Conjugate

Trt-Cl resin and Fmoc amino acids were purchased from GL Biochem (Shanghai, China). A coupling reagent and a cleavage cocktail reagent were purchased from Sigma Aldrich, and other solvents were purchased from Daejung Chemical (Korea).

A peptide was synthesized by Fmoc solid phase peptide synthesis (SPPS) using ASP48S (Peptron, Inc., Korea). Through this, the peptide FRRG (SEQ ID NO 1) was synthesized.

The synthesized peptide was purified by reversed-phase HPLC (Shimadzu Prominence HPLC, Japan) using a Vydac Everest C18 column (250 mm×22 mm, 10 µm, USA). Elution was conducted using a water-acetonitrile linear gradient (10-75% (v/v) of acetonitrile) containing 0.1% (v/v) trifluoroacetic acid. The purified peptide was subjected to molecular weight measurement by LC/MS (Shimadzu LC/MS-2020 series, Japan) and then freeze-dried using FDT12012 (Operon, Korea).

1) Synthesis of Amphiphilic Peptide (FRRG)

A peptide was synthesized according to the standard solid phase peptide synthesis protocol. The peptide with the amino acid sequence FRRG (SEQ ID NO 1) was synthesized using the ASP48S peptide synthesizer (Peptron, Inc., Korea). A standard amino acid-protecting group (Fmoc) was used for the synthesis.

Specifically, after rocking twice with DMF containing 20% piperidine for 10 minutes in order to remove the Fmoc protecting group, coupling was conducted for 2 hours in a DMF solvent using Fmoc amino acids (8 eq), HOBT (8 eq), HBTU (8 eq) and DIPEA (16 eq). In each step, the resin was washed twice with DMF and methanol.

After the peptide with a desired sequence was synthesized, reaction was conducted for 2 hours using a TFA/EDT/thioanisole/TIS/DW solution (90/2.5/2.5/2.5/2.5 volume) in order to separate the crude peptide from the resin. The solution was precipitated in cold ether and pellets were separated by centrifugation. The pellets were obtained as powder through an evaporation process.

The obtained crude peptide was dissolved in distilled water and then purified by reversed-phase HPLC using a C18 column. Elution was conducted using a water-acetonitrile linear gradient (10-75% (v/v) of acetonitrile) containing 0.1% (v/v) trifluoroacetic acid. The purified peptide was freeze-dried and stored.

2) Synthesis of FRRG-DOX Drug Conjugate

After dissolving the amphiphilic peptide FRRG prepared in the step 1) in water and adding doxorubicin, the mixture was stirred for 24 hours at room temperature. The obtained peptide was purified by reversed-phase HPLC (water-acetonitrile, 0.1% TFA).

For analysis of chemical structure of doxorubicin, the FRRG peptide and the drug conjugate (FRRG-DOX) formed therefrom, they were dissolved in DMSO-$d_6$ and characteristic peaks were investigated by 600 MHz $^1$H-NMR (DD 2600 MHz FT NMR, Agilent Technologies, USA). The molecular weights of FRRG-DOX and G-DOX (peptide fragment cleaved from FRRG-DOX) were analyzed by MALDI (matrix-assisted laser desorption/ionization) (AB Sciex TOF/TOF 5800 System, USA) (with cyano-4-hydroycinnamic acid matrix).

Example 1

Preparation of Formulated Drug Conjugate (FDOX)

In order to improve the in-vivo stability of the drug conjugate synthesized in Preparation Example 1, the drug conjugate and pluronic F68 were mixed (simple mixing) in an aqueous solution. Although the drug conjugate forms spherical nanoparticles in an aqueous solution through self-assembly, the polymer-based nanodrug was prepared using pluronic F68 because the nanoparticles are unstable in vivo.

Specifically, the FRRG-DOX drug conjugate (21 mg) and the pluronic F68 (9 mg) were dispersed in 5 mL of triply distilled water, respectively. After slowly dropping the aqueous solution wherein the pluronic F68 was dispersed onto the aqueous solution wherein the FRRG-DOX was dispersed and stirring for 4 hours, a formulated drug conjugate (FDOX) was obtained as red powder through freeze drying.

Test Example 1

Figure 2:
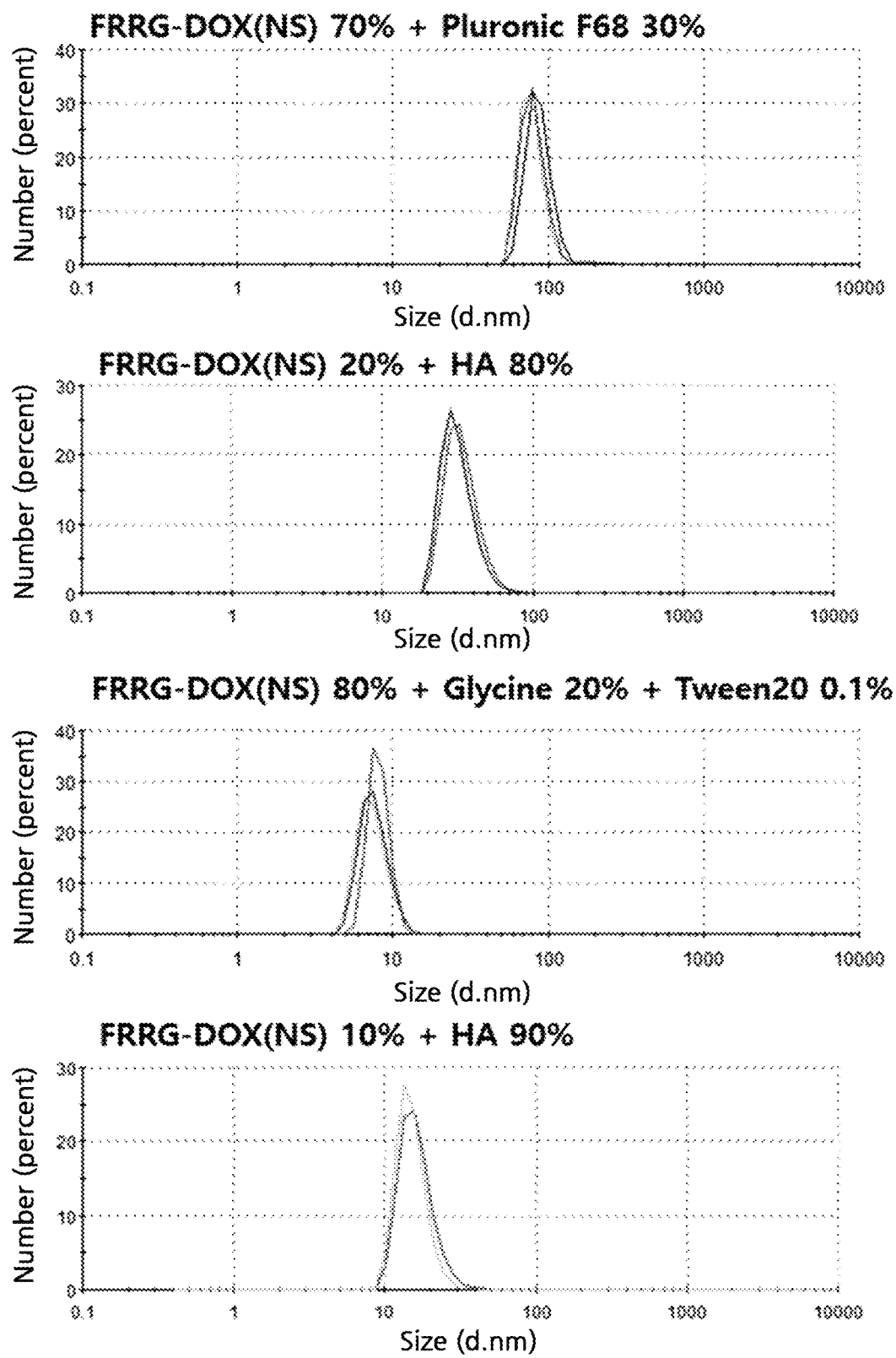
FIG. 2 shows a result of measuring the average diameter and dispersity (PDI) of particles formed when drug conjugates are formulated with different additives.

Analysis of Particle Size and Dispersity Depending on Formulation of Drug Conjugate The average diameter and dispersity (PDI) of particles of formulated using various additives to improve the stability of the drug conjugate prepared in Preparation Example 1 were measured, and the result is shown in Table 1 and FIG. 2. In Table 1, F68 stands for pluronic F68, HA for hyaluronic acid, and Tween 20 for polysorbate 20.

TABLE 1

|  |  | 1 | 2 | 3 | 4 |
|---|---|---|---|---|---|
| Drug conjugate of Preparation Example 1 |  | 21 mg | 21 mg | 21 mg | 21 mg |
| Additive | F68 | 9 mg | — | — | — |
|  | HA | — | 84 mg | — | 189 mg |
|  | Glycine | — | — | 5.25 mg | — |
|  | Tween 20 | — | — | 0.026 mg | — |
| Average diameter |  | 91.33 nm | 34.7 nm | 13.45 nm | 21.13 nm |
| PDI |  | 0.184 | 0.287 | 0.354 | 0.303 |

FIG. 2 shows a result of measuring the average diameter and dispersity (PDI) of the particles formed when the drug conjugate was formulated with different additives. FIG. 2 shows the result for 1 (FRRG-DOX+Pluronic F68), 2 (FRRG-DOX+HA80), 3 (FRRG-DOX+glycine+Tween 20) and 4 (FRRG-DOX+HA90) in sequence.

From Table 1 and FIG. 2, it can be seen that F68 having a size of 80-200 nm and a dispersity below 0.2 is the most preferred to expect the most stable tumor accumulation efficiency when the drug conjugate is formulated. If the size is smaller than 80 nm, the drug conjugate may not be degraded easily in vivo due to due to insufficient stability. And, if the dispersity is 0.2 or higher, accurate dosage control may be difficult due to non-uniformity.

Test Example 2

Evaluation of Tumor-Treating Effect of Pharmaceutical Composition for Combination Therapy Containing Formulated Drug Conjugate (FDOX) and Anti-PD-L1 Antibody In Vivo The tumor-treating effect of the pharmaceutical composition for combination therapy containing the formulated drug conjugate (FDOX) and the anti-PD-L1 antibody in vivo was evaluated. Specifically, athymic nude mice (6-week-old, 20-25 g, male) purchased from Nara Bio (Gyenggi-do, Korea) were used. In order to express colorectal cancers in the male nude mice, a tumor animal model was prepared by subcutaneously inoculating $1\times10^7$ HT-29 colorectal cancer cells into left thighs. Experiment was conducted when the tumor size reached about 100-120 mm$^3$ (see FIG. 1). The formulated drug conjugate (FDOX) was administered intravenously at a concentration of 4 mg/kg, and the anti-PD-L1 antibody was administered intraperitoneally at a concentration of 10 mg/kg. A test group (FDOX+PD-L1 Ab) was prepared by administering the two therapeutic agents at 3-day intervals.

The following comparison groups were prepared to compare the efficiency of the test group.

Control group (control): identical to the test group except that no drug was administered.

First comparison group (FDOX): identical to the test group except that only the formulated drug conjugate (FDOX) was administered without the anti-PD-L1 antibody.

Second comparison group (DOX+PD-L1 Ab): identical to the test group except that 4 mg/kg of doxorubicin was administered intravenously instead of the formulated drug conjugate (FDOX).

Third comparison group (DOX): identical to the test group except that 4 mg/kg doxorubicin was administered alone instead of the co-administration of the formulated drug conjugate (FDOX) and the anti-PD-L1 antibody.

Fourth comparison group (PD-L1 Ab): identical to the test group except that 10 mg/kg anti-PD-L1 antibody was intraperitoneally administered alone instead of the co-administration of the formulated drug conjugate (FDOX) and the anti-PD-L1 antibody.

For the test group, the control group and the first, second and third comparison groups, tumor size was measured at 2-day intervals and calculated as maximum diameter×minimum diameter. In addition, the body weight of each group was measured at 2-day intervals to investigate in-vivo toxicity.

Figure 3:
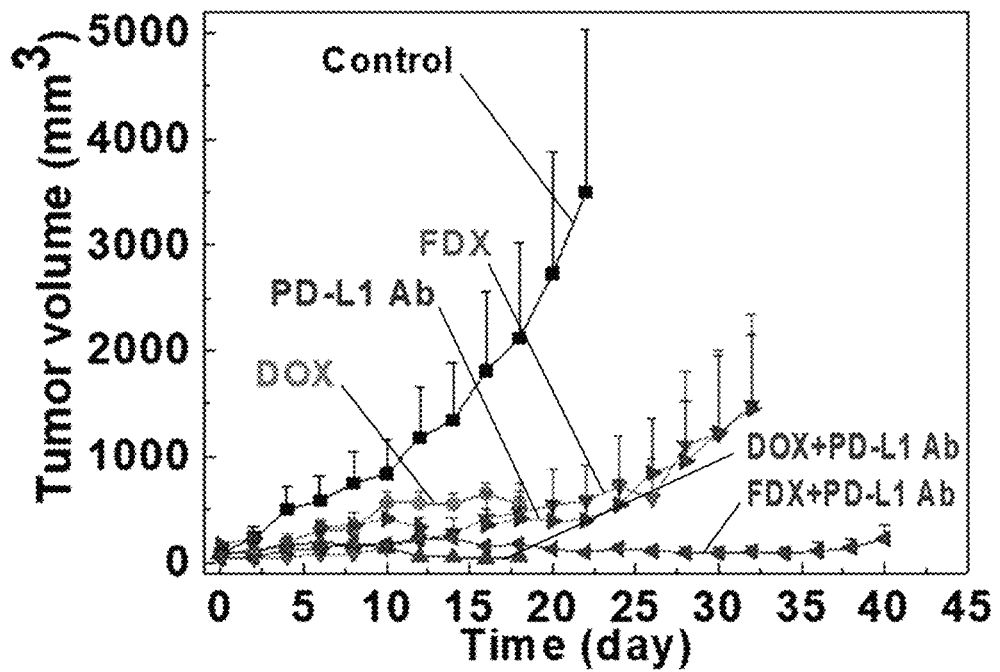
FIG. 3 shows a result of analyzing tumor-treating effect in vivo for co-administration of a formulated drug conjugate (FDOX) and an anti-PD-L1 antibody by measuring tumor volume depending on time.

FIG. 3 shows a result of analyzing the tumor-treating effect in vivo for co-administration of the formulated drug conjugate (FDOX) and the anti-PD-L1 antibody by measuring tumor volume depending on time.

From FIG. 3, it can be seen that tumor growth was inhibited consistently and completely in the test group (FDOX+PD-L1 Ab) co-administered with the formulated drug conjugate (FDOX) and the anti-PD-L1 antibody.

In contrast, when the drug conjugate or the anti-PD-L1 antibody was administered alone as in the first and fourth comparison groups, the tumor growth was delayed but was not completely inhibited. As a result, the tumor continued to grow with time, reaching a tumor size of 1000 mm$^3$ or larger 25 days later.

In addition, when the anticancer agent was used alone or when the anti-PD-L1 antibody was co-administered with another anticancer agent as in the second and third comparison groups, tumor growth could be delayed but could not be completely inhibited. In addition, fatal side effect leading to death was observed due to in-vivo toxicity.

Figure 4:
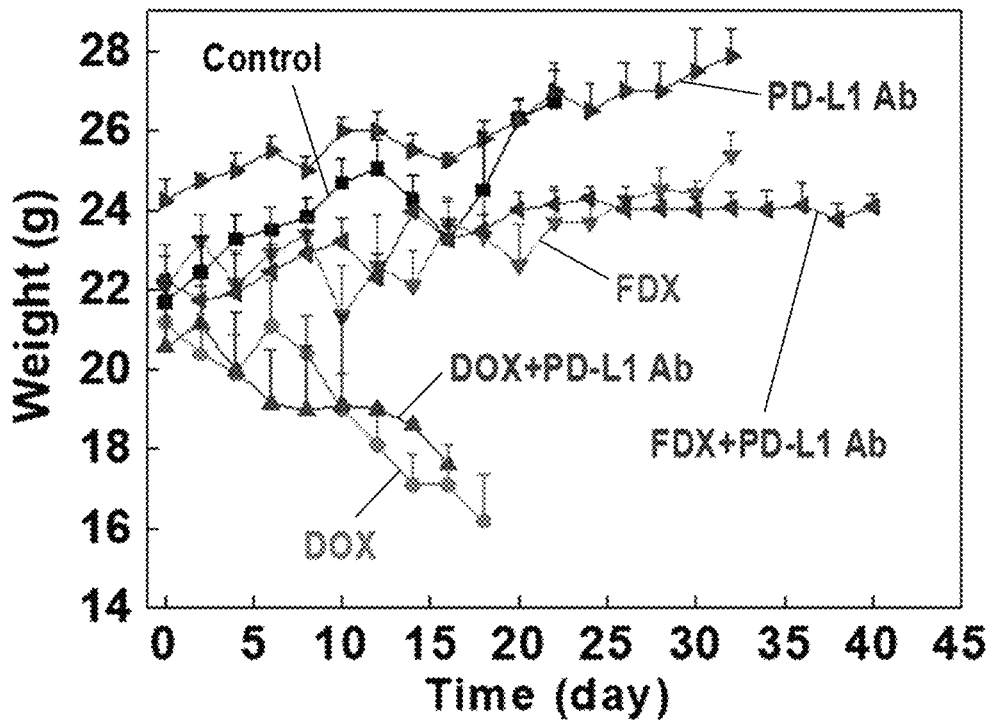
FIG. 4 shows a result of analyzing in-vivo toxicity for co-administration of a formulated drug conjugate (FDOX) and an anti-PD-L1 antibody by measuring body weight (g) depending on time.

FIG. 4 shows a result of analyzing in-vivo toxicity for the co-administration of the formulated drug conjugate (FDOX) and the anti-PD-L1 antibody by measuring body weight (kg) depending on time.

From FIG. 4, it can be seen that there was little change in body weight in the test group (FDOX+PD-L1 Ab) co-administered with the formulated drug conjugate (FDOX) and the anti-PD-L1 antibody and the first comparison group (FDOX). When the anti-PD-L1 antibody was administered alone as in the fourth comparison group, the body weight was increased consistently as in the control group.

In contrast, when the anticancer agent was used alone or when the anti-PD-L1 antibody was co-administered with another anticancer agent as in the second and third comparison groups, the body weight was decreased rapidly and the mice died within 20 days.

Accordingly, it can be seen that, whereas the co-administration of the formulated drug conjugate (FDOX) and the anti-PD-L1 antibody according to the present disclosure does not exhibit systemic toxicity, the use of the anticancer agent alone or the co-administration of the anti-PD-L1 antibody and the anticancer agent can lead to systemic toxicity.

Test Example 3

Evaluation of Immunotherapeutic Effect of Co-Administration of Formulated Drug Conjugate (FDOX) and Anti-PD-L1 Antibody In Vivo For evaluation of the immunotherapeutic effect of the co-administration of the formulated drug conjugate (FDOX) and the anti-PD-L1 antibody in vivo, a test group, a control group and first, second, third and fourth comparison groups were prepared as in Test Example 1, and cancerous tissues were extracted therefrom. For the animal models of the second and third comparison groups, cancerous tissues were extracted on day 20 after the drug administration because the animals died within 20 days. Substances other than cells were removed from the extracted cancerous tissues using a cell separation kit. The recovered cells were stained with CD45 antibody which labels immune cells and CD8 which labels T cells and analyzed by flow cytometry.

Figure 5:
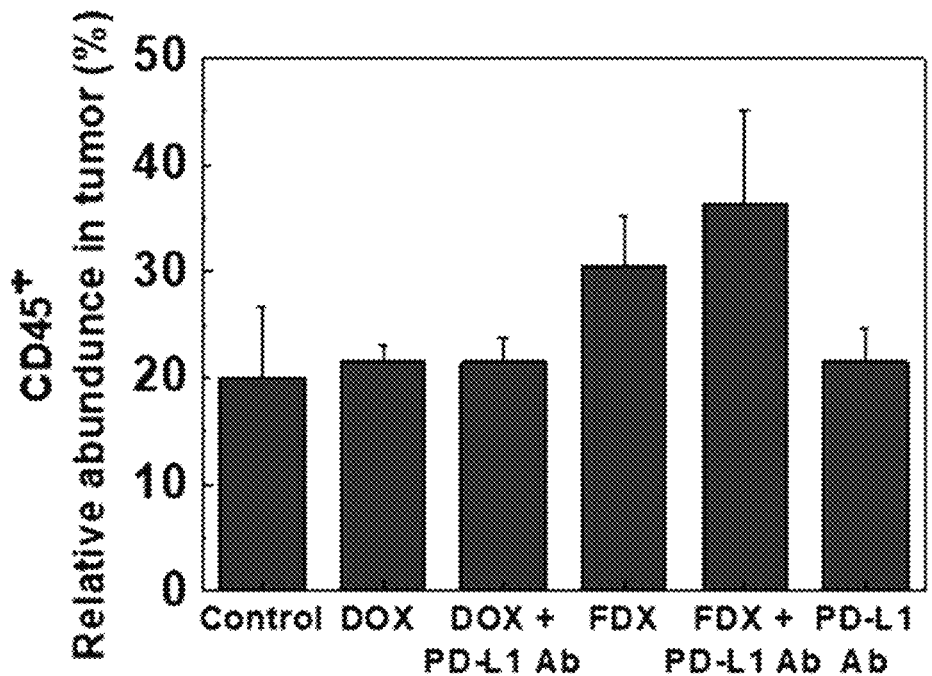
FIG. 5 shows a result of analyzing the activation of immune cells by co-administration of a formulated drug conjugate (FDOX) and an anti-PD-L1 antibody by analyzing the proportion of immune cells expressing CD45 in cancerous tissues isolated from each group by flow cytometry.

FIG. 5 shows a result of analyzing the activation of immune cells by the co-administration of the formulated drug conjugate (FDOX) and the anti-PD-L1 antibody by analyzing the proportion of immune cells expressing CD45 in the cancerous tissues isolated from each group by flow cytometry.

Figure 6:
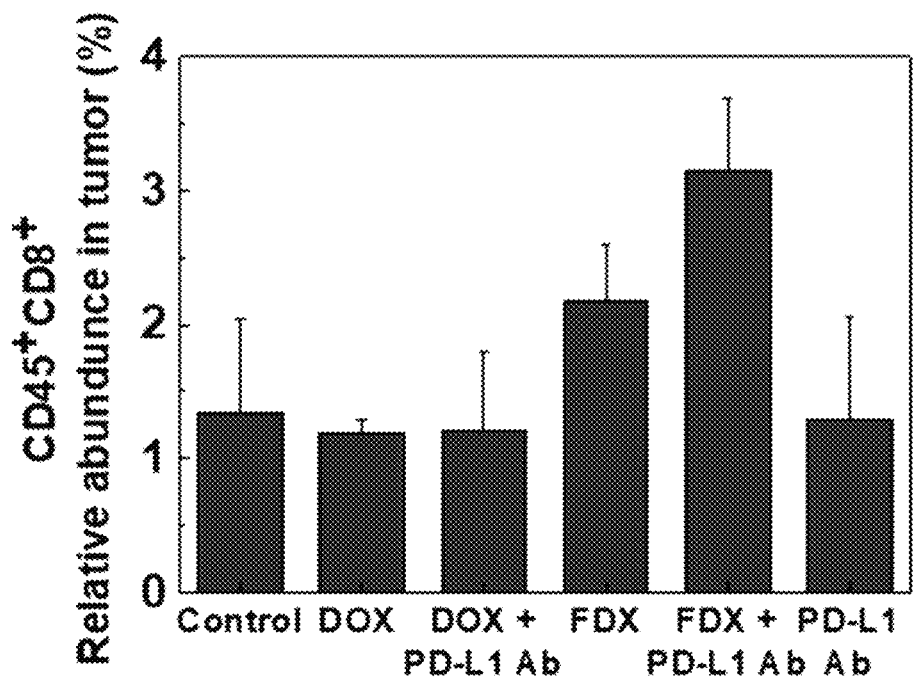
FIG. 6 shows a result of analyzing the activation of immune cells by co-administration of a formulated drug conjugate (FDOX) and an anti-PD-L1 antibody by analyzing the proportion of immune cells expressing CD8 in cancerous tissues isolated from each group by flow cytometry.

FIG. 6 shows a result of analyzing the activation of immune cells by the co-administration of the formulated drug conjugate (FDOX) and the anti-PD-L1 antibody by analyzing the proportion of immune cells expressing CD8 in the cancerous tissues isolated from each group by flow cytometry.

As shown in FIG. 5 and FIG. 6, the first comparison group to which only the formulated drug conjugate (FDOX) was administered and the test group co-administered with the anti-PD-L1 antibody showed increased immune cells in the cancerous tissues as compared to the third comparison group to which only the existing anticancer agent (doxorubicin; DOX) was administered. This may be because the formulated drug conjugate results in increased cell death due to superior accumulation efficiency in tumors as compared to when only the anticancer agent was administered, and the cell death leads to immunogenic cell death. As a result, immune cells are increased significantly in the animal model to which the formulated drug conjugate with superior accumulation efficiency in tumors was administered.

In contrast, although the fourth comparison group to which only the anti-PD-L1 antibody was administered showed no increase in immune cells at all, the test group co-administered with the formulated drug conjugate (FDOX) and the anti-PD-L1 antibody showed significantly remarkable increase in immune cells as compared to the first comparison group.

That is to say, it can be seen that the co-administration of the formulated drug conjugate (FDOX) and the anti-PD-L1 antibody according to the present disclosure provides remarkable immune cell-activating effect beyond the sum of the effects expected from the single administrations thereof.

Test Example 4

Evaluation of Toxicity of Co-Administration of Formulated Drug Conjugate (FDOX) and Anti-PD-L1 Antibody For evaluation of the immunotherapeutic effect of the co-administration of the formulated drug conjugate (FDOX) and the anti-PD-L1 antibody in vivo, a test group, a control group and first, second, third and fourth comparison groups were prepared as in Test Example 2 and major organs (heart, kidney, spleen, lung and liver) were extracted therefrom. For the animal models of the second and third comparison groups, the organs were extracted on day 20 after the drug administration because the animals died within 20 days. After preparing tissues of each extracted organ into 10-μm thick sections, cell death in the organ was evaluated by staining cancerous tissues with annexin V. In addition, the tissues extracted from the major organs (heart, kidney, spleen, lung and liver) were stained with hematoxylin and eosin for investigation of the structural change in the tissues and toxicity.

Figure 7:
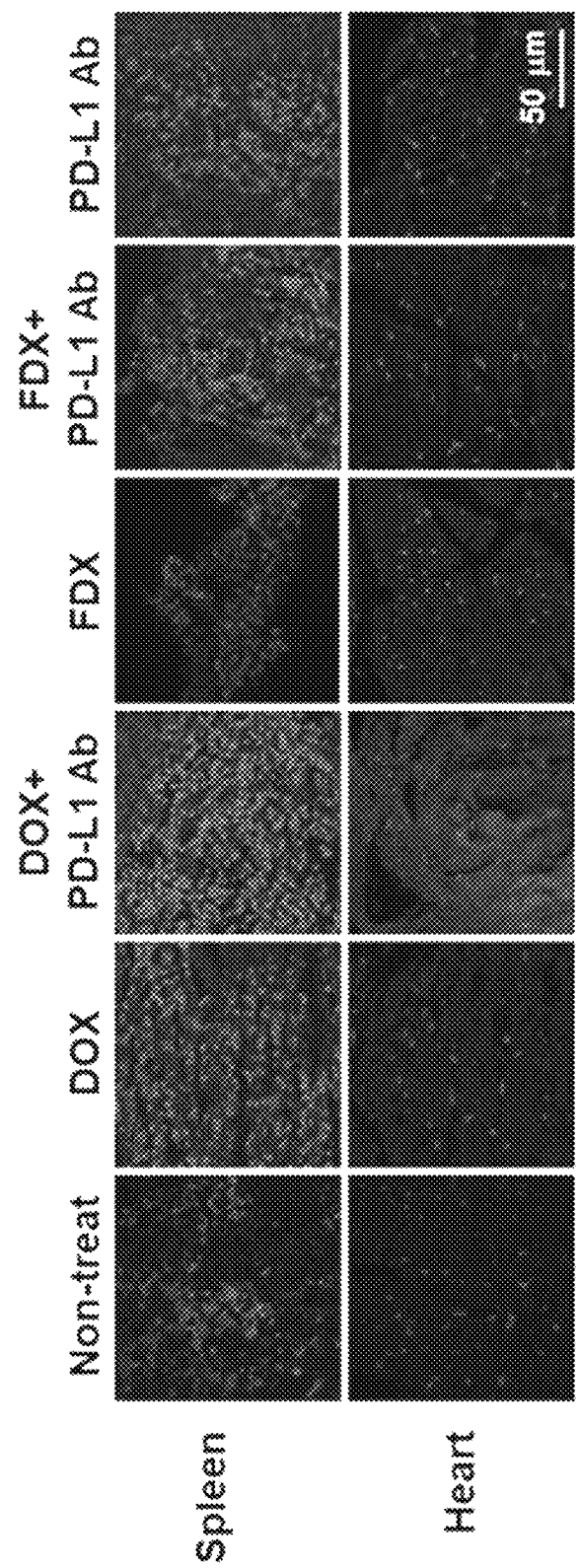
FIG. 7 shows a result of analyzing cell death in tissues by co-administration of a formulated drug conjugate (FDOX) and an anti-PD-L1 antibody by staining tissues isolated from each group with annexin V and imaging them with a fluorescence microscope.

FIG. 7 shows a result of analyzing cell death in the tissues by the co-administration of the formulated drug conjugate (FDOX) and the anti-PD-L1 antibody by staining the tissues isolated from each group with annexin V and imaging them with a fluorescence microscope.

Figure 8:
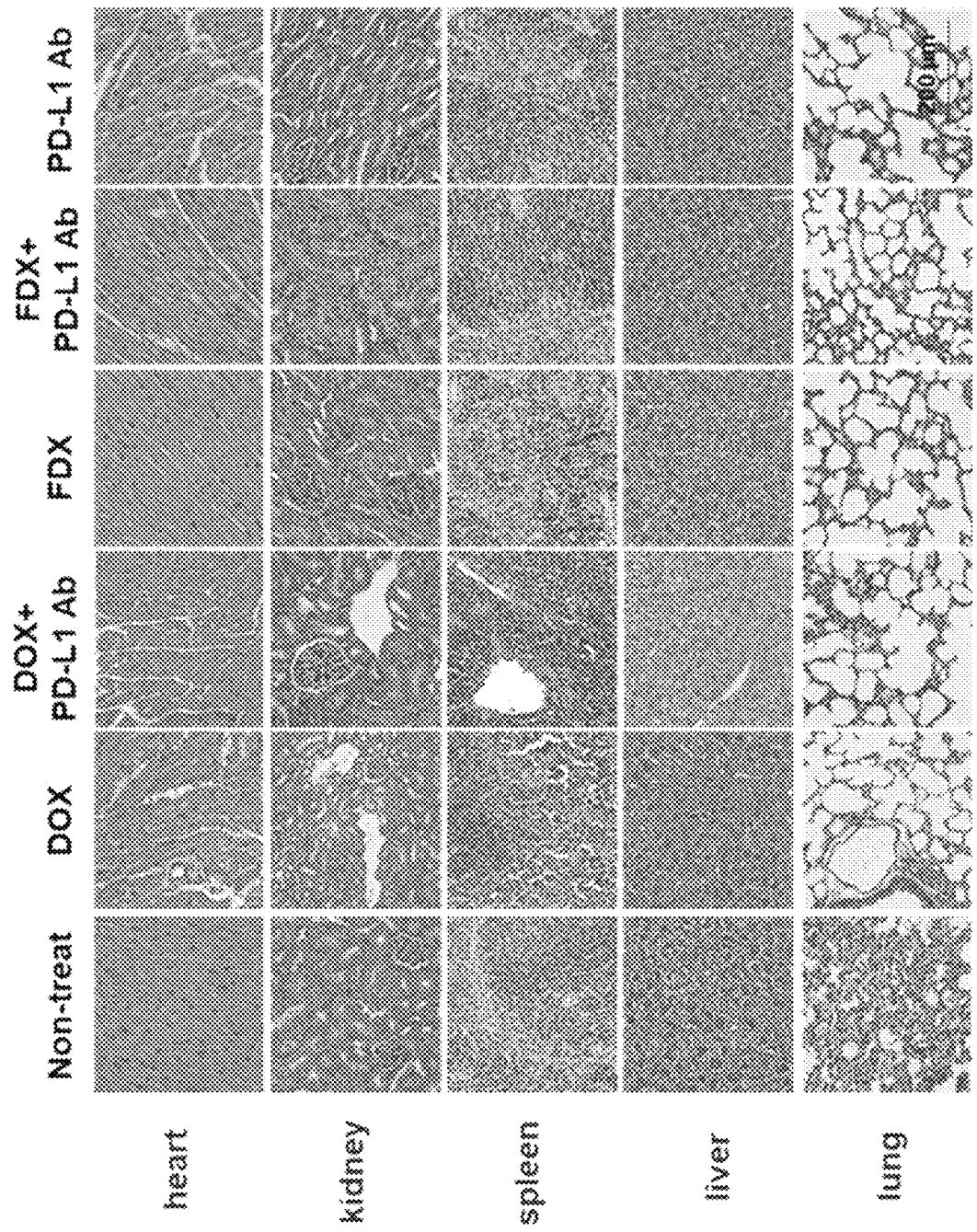
FIG. 8 shows a result of analyzing cell death in major organs (heart, kidney, spleen, lung and liver) by co-administration of a formulated drug conjugate (FDOX) and an anti-PD-L1 antibody by staining major organs isolated from each group with H&E.

FIG. 8 shows a result of analyzing the cell death in the major organs (heart, kidney, spleen, lung and liver) by the co-administration of the formulated drug conjugate (FDOX) and the anti-PD-L1 antibody by staining major organs isolated from each group with H&E.

As shown in FIG. 7, the co-administration of the formulated drug conjugate (FDOX) and the anti-PD-L1 antibody (test group) resulted in the most cell death (green) of spleen tissue (colorectal cancer tissue). In contrast, no cell death was induced in the heart issue.

In addition, no cell death was observed in the spleen tissue and the large intestine tissue for the formulated drug conjugate (FDOX, first comparison group).

As shown in FIG. 8, the co-administration of the formulated drug conjugate (FDOX) and the anti-PD-L1 antibody (test group) resulted in no significant change in the major organs as compared to the control group.

In contrast, the single administration of doxorubicin (third comparison group) or the co-administration of doxorubicin and the anti-PD-L1 antibody (second comparison group) resulted in long-term toxicity such as hemorrhage, disruption of tissue structure, enucleation, etc. in the major organs.

What is claimed is:

1. A method for treating cancer comprising administering a therapeutically effective amount of a first pharmaceutical ingredient comprising a drug conjugate wherein an anticancer agent is bound at one end of an amphiphilic peptide represented by SEQ ID NO 1 and a poloxamer; and a second pharmaceutical ingredient comprising an anti-PD-L1 antibody; to human or a non-human mammal.

2. The method according to claim 1, wherein the cancer is colorectal cancer.

3. The method according to claim 1, wherein the first pharmaceutical ingredient is administered intravenously and the second pharmaceutical ingredient is administered intraperitoneally.

4. A method for inhibiting growth, metastasis or recurrence of colorectal cancer cells by killing colorectal cancer cells and activating immune cells around the colorectal cancer cells, comprising a step of administering a therapeutically effective amount of a first pharmaceutical ingredient containing a drug conjugate wherein an anticancer agent is bound at one end of an amphiphilic peptide represented by SEQ ID NO 1 and a poloxamer; and a second pharmaceutical ingredient containing an anti-PD-L1 antibody; to human or a non-human mammal.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
```

<223> OTHER INFORMATION: amphiphilic peptides

<400> SEQUENCE: 1

Phe Arg Arg Gly
1

<210> SEQ ID NO 2
<211> LENGTH: 290
<212> TYPE: PRT
<213> ORGANISM: Homo sapiens

<400> SEQUENCE: 2

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 3
<211> LENGTH: 272
<212> TYPE: PRT
<213> ORGANISM: Homo sapiens

<400> SEQUENCE: 3

-continued

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20              25                  30

Ala Ala Leu Ile Val Tyr Trp Glu Met Glu Asp Lys Asn Ile Ile Gln
            35              40                  45

Phe Val His Gly Glu Glu Asp Leu Lys Val Gln His Ser Ser Tyr Arg
        50              55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270
```